(12) United States Patent
Begg et al.

(10) Patent No.: US 11,413,057 B2
(45) Date of Patent: Aug. 16, 2022

(54) TISSUE RESECTING INSTRUMENTS INCLUDING AUXILIARY VACUUM FEATURES

(71) Applicant: Covidien LP, Mansfield, MA (US)

(72) Inventors: Nikolai D. Begg, Wellesley, MA (US); Dale E. Whipple, Nashua, NH (US)

(73) Assignee: Covidien LP, Mansfield, MA (US)

( * ) Notice: Subject to any disclaimer, the term of this patent is extended or adjusted under 35 U.S.C. 154(b) by 254 days.

(21) Appl. No.: 16/891,707

(22) Filed: Jun. 3, 2020

(65) Prior Publication Data

US 2020/0405338 A1 Dec. 31, 2020

Related U.S. Application Data

(60) Provisional application No. 62/867,278, filed on Jun. 27, 2019.

(51) Int. Cl.
*A61B 17/32* (2006.01)
*A61B 17/42* (2006.01)
*A61B 17/3207* (2006.01)
*A61B 17/00* (2006.01)

(52) U.S. Cl.
CPC ........ *A61B 17/32002* (2013.01); *A61B 17/42* (2013.01); *A61B 17/320783* (2013.01); *A61B 2017/00367* (2013.01); *A61B 2017/320028* (2013.01); *A61B 2017/4216* (2013.01); *A61B 2217/005* (2013.01)

(58) Field of Classification Search
CPC ...... A61B 17/32002; A61B 17/320783; A61B 2017/320024; A61B 2017/320028; A61B 2017/320032; A61B 2017/00367; A61B 2017/4216; A61B 2217/005; A61B 10/0275; A61B 10/0283
See application file for complete search history.

(56) References Cited

U.S. PATENT DOCUMENTS

| | | | |
|---|---|---|---|
| 5,403,276 A | | 4/1995 | Schechter et al. |
| 5,617,874 A | * | 4/1997 | Baran ................ A61B 10/0275 600/558 |
| 5,782,795 A | | 7/1998 | Bays |
| 5,972,012 A | * | 10/1999 | Ream ............... A61B 17/32002 604/22 |
| 8,012,153 B2 | | 9/2011 | Woloszko et al. |
| 8,986,334 B2 | | 3/2015 | Mark et al. |

(Continued)

*Primary Examiner* — Wade Miles
(74) *Attorney, Agent, or Firm* — Carter, DeLuca & Farrell LLP

(57) ABSTRACT

A tissue resecting instrument includes a drive assembly coupled to an inner cutting shaft and configured to drive translation and/or rotation of the inner cutting shaft, a trigger coupled to the drive assembly and configured for manual actuation to drive the drive assembly, a vacuum generator configured to generate vacuum to suction cut tissue through the inner cutting shaft and into the vacuum generator, and a tissue collection cartridge configured to engage the housing. The tissue collection cartridge defines a port configured to communicate with the vacuum generator such that the vacuum generator urges cut tissue from the vacuum generator through the port into the tissue collection cartridge. An auxiliary vacuum source is configured to selectively provide additional vacuum to increase suctioning of cut tissue through the inner cutting shaft and into the vacuum generator.

20 Claims, 4 Drawing Sheets

(56) References Cited

U.S. PATENT DOCUMENTS

| | | | |
|---|---|---|---|
| 9,060,760 B2 | 6/2015 | Sullivan et al. | |
| 9,107,691 B2 | 8/2015 | Fojtik | |
| 9,486,233 B2 | 11/2016 | Bek et al. | |
| 9,913,629 B1 | 3/2018 | Sullivan et al. | |
| 10,022,140 B2 | 7/2018 | Germain et al. | |
| 10,335,127 B2 * | 7/2019 | Shabaz | A61B 10/0275 |
| 2005/0209622 A1 | 9/2005 | Garrison | |
| 2007/0213755 A1 | 9/2007 | Beckman et al. | |
| 2009/0270895 A1 | 10/2009 | Churchill et al. | |
| 2010/0152611 A1 | 6/2010 | Parihar et al. | |
| 2010/0312140 A1 | 12/2010 | Smith et al. | |
| 2011/0152715 A1 * | 6/2011 | Delap | A61B 10/0275 600/566 |
| 2011/0208086 A1 * | 8/2011 | Hibner | A61B 10/0275 600/566 |
| 2012/0109007 A1 * | 5/2012 | Rhad | A61B 10/0096 600/567 |
| 2012/0172888 A1 * | 7/2012 | Shugrue | A61B 17/32002 606/119 |
| 2013/0172870 A1 | 7/2013 | Germain et al. | |
| 2013/0211321 A1 | 8/2013 | Dubois et al. | |
| 2015/0305765 A1 | 10/2015 | Fojtik et al. | |
| 2017/0049441 A1 | 2/2017 | Sauer et al. | |
| 2017/0105607 A1 | 4/2017 | Truckai | |
| 2017/0105736 A1 | 4/2017 | Chen et al. | |
| 2017/0333119 A1 | 11/2017 | Truckai | |
| 2018/0103939 A1 * | 4/2018 | Van Liere | A61B 10/0283 |
| 2018/0136091 A1 * | 5/2018 | Ryan | G01N 1/08 |
| 2019/0105023 A1 * | 4/2019 | Aljuri | A61B 10/02 |
| 2020/0330081 A1 * | 10/2020 | Vetter | A61B 10/0275 |

\* cited by examiner

TISSUE RESECTING INSTRUMENTS INCLUDING AUXILIARY VACUUM FEATURES

CROSS REFERENCE TO RELATED APPLICATIONS

This application claims the benefit of U.S. Provisional Application Ser. No. 62/867,278, filed Jun. 27, 2019, the entire contents of which are incorporated by reference herein.

FIELD

The present disclosure relates generally to the field of tissue resection. In particular, the present disclosure relates to tissue resecting instruments including auxiliary vacuum features.

BACKGROUND

Tissue resecting instruments are commonly used in endoscopic tissue resection procedures within an organ, such as a uterus, by inserting an endoscope (or hysteroscope) into the uterus and passing the tissue resection instrument through the endoscope (or hysteroscope) and into the uterus. With respect to such endoscopic tissue resection procedures, tissue is resected at the surgical site and suctioned proximally through the tissue resecting instrument, along with fluid at the surgical site.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a tissue resecting instrument including a housing, an outer shaft, an inner cutting shaft, a drive assembly, a trigger, a vacuum generator, and a tissue collection cartridge. The outer shaft extends distally from the housing and defines a window at a distal end portion thereof. The inner cutting shaft extends through the outer shaft and is configured to translate and/or rotate relative to the outer shaft to cut tissue extending through the window. The drive assembly is coupled to the inner cutting shaft and configured to drive the translation and/or rotation of the inner cutting shaft. The trigger is coupled to the drive assembly such that manual actuation of the trigger actuates the drive assembly to drive the translation and/or rotation of the inner cutting shaft. The vacuum generator is coupled to the drive assembly and the inner cutting shaft such that, during a first portion of the actuation of the drive assembly, the vacuum generator is configured to generate vacuum to suction cut tissue through the inner cutting shaft and into the vacuum generator. The tissue collection cartridge is configured to releasably engage the housing and defines a port configured to communicate with the vacuum generator such that, during a second portion of the actuation of the drive assembly, the vacuum generator urges cut tissue from the vacuum generator through the port into the tissue collection cartridge. An auxiliary vacuum source is configured to selectively provide additional vacuum to increase suctioning of cut tissue through the inner cutting shaft and into the vacuum generator.

In aspects of the present disclosure, the trigger is pivotably coupled to the housing and movable relative thereto between an un-actuated position and an actuated position to drive the drive assembly to translate the inner cutting shaft between a more-proximal position and a more-distal position. In such aspects, the first portion of the actuation of the drive assembly may correspond to movement of the trigger from the un-actuated position to the actuated position. Additionally or alternatively, the second portion of the actuation of the drive assembly may correspond to movement of the trigger from the actuated position to the un-actuated position.

In aspects of the present disclosure, the auxiliary vacuum source is disposed on or within the housing. The auxiliary vacuum source, in aspects, is alternatively or additionally configured to releasably couple to the housing.

In aspects of the present disclosure, the auxiliary vacuum source includes a vacuum accumulator. Alternatively, the auxiliary vacuum source includes a vacuum pump.

In aspects of the present disclosure, the auxiliary vacuum source is a vacuum accumulator coupled to the vacuum generator and configured to accumulate vacuum. The vacuum accumulator is configured to selectively release the accumulated vacuum to provide additional vacuum to increase suctioning of cut tissue through the inner cutting shaft and into the vacuum generator.

In aspects of the present disclosure, the vacuum accumulator includes an accumulator tank configured to accumulate vacuum therein and a release actuator configured to release the accumulated vacuum to provide the additional vacuum.

In aspects of the present disclosure, a manipulatable valve is disposed between the accumulator tank and the vacuum generator. In such aspects, the release actuator is configured to transition the manipulatable valve to a bi-directional, open configuration to provide the additional vacuum.

In aspects of the present disclosure, the vacuum accumulator is configured to incrementally accumulate vacuum upon each actuation of the drive assembly.

In aspects of the present disclosure, the auxiliary vacuum source is a supplemental vacuum configured to releasably couple to the vacuum generator. The supplemental vacuum is selectively activatable to provide additional vacuum to increase suctioning of cut tissue through the inner cutting shaft and into the vacuum generator.

In aspects of the present disclosure, the supplemental vacuum includes a vacuum pump.

In aspects of the present disclosure, the supplemental vacuum further includes a fluid line extending from the vacuum pump to a first connector. The first connector is configured to releasably couple to a second connector associated with the housing to thereby couple the vacuum pump with the vacuum generator.

In aspects of the present disclosure, a one-way valve is disposed between the supplemental vacuum and the vacuum generator.

In aspects of the present disclosure, the supplemental vacuum is configured to provide the additional vacuum to the chamber of the vacuum generator.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1:
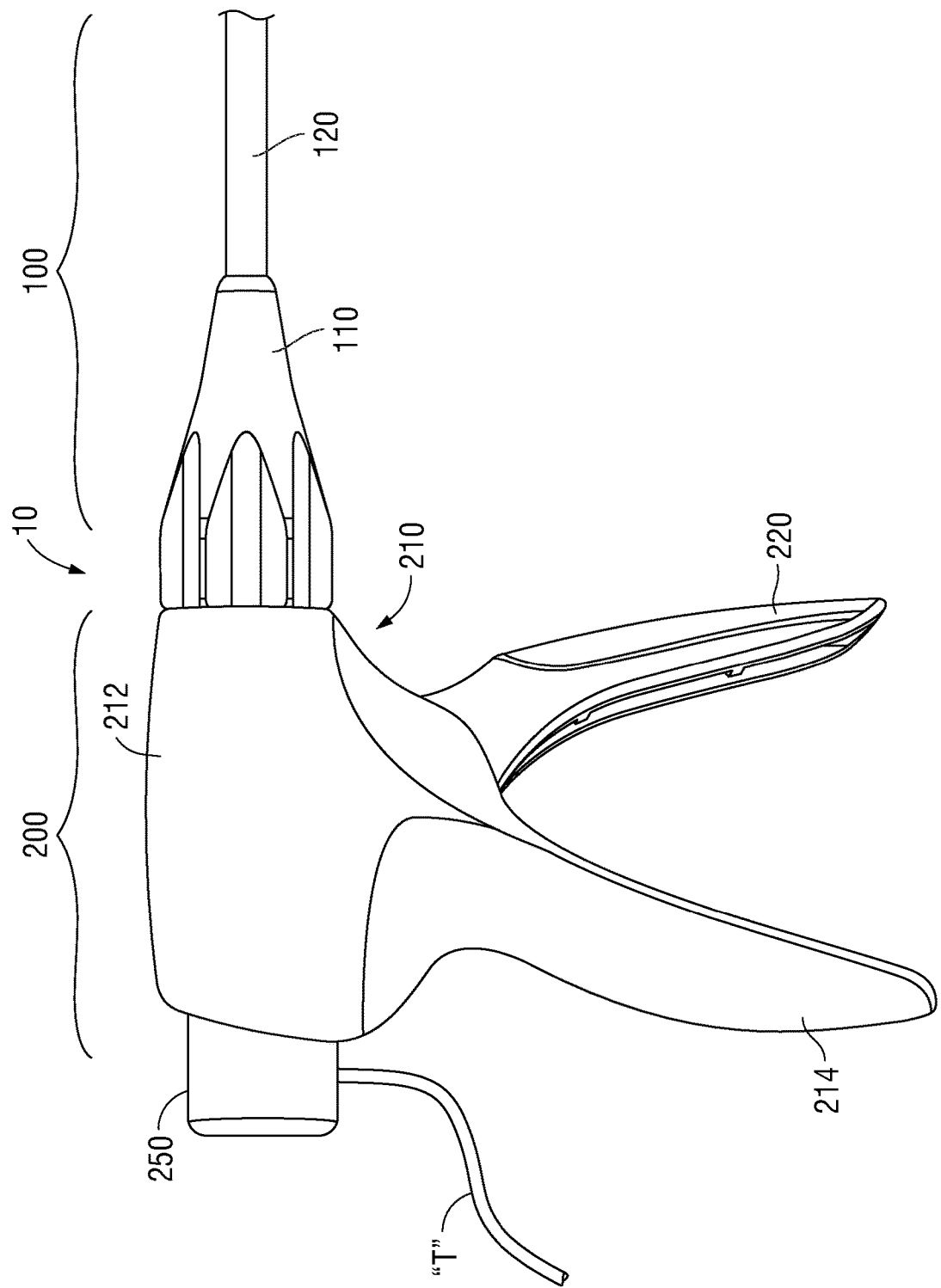
FIG. 1 is a perspective view of a proximal portion of a tissue resecting instrument provided in accordance with the present disclosure.

Referring generally to FIG. 1, a tissue resecting instrument 10 provided in accordance with the present disclosure configured for manual actuation to resect and remove tissue includes an end effector assembly 100 and a handpiece assembly 200. Tissue resecting instrument 10 may be adapted to connect to a fluid collection reservoir (not shown) via outflow tubing "T" for collecting fluid suctioned through tissue resecting instrument 10 during use or, alternatively, may be configured to internally retain the fluid suctioned therethrough, e.g., via internal outflow tubing and an internal fluid collection reservoir (not shown). As an alternative to manual actuation, tissue resecting instrument 10 may incorporate or couple to a powered drive source (not shown), e.g., a motor, for powered actuation thereof.

With continued reference to FIG. 1, tissue resecting instrument 10 may be configured as a single-use instrument that is discarded after use or sent to a manufacturer for reprocessing, a reusable instrument capable of being cleaned and/or sterilized for repeated use by the end-user, or a partially-single-use, partially-reusable instrument. With respect to partially-single-use, partially-reusable configurations, handpiece assembly 200 may be configured as a cleanable/sterilizable, reusable component, while end effector assembly 100 is configured as a single-use, disposable/reprocessable component, or vice versa. In any of the above configurations, end effector assembly 100 may be configured to releasably engage handpiece assembly 200 to facilitate disposal/reprocessing of any single-use components and cleaning and/or sterilization of any reusable components. Further, enabling releasable engagement of end effector assembly 100 with handpiece assembly 200 allows for use of different end effector assemblies, e.g., end effector assembly 100 (FIGS. 2A and 2B) or end effector assembly 1100 (FIGS. 3A and 3B), with handpiece assembly 200. In other embodiments, end effector assembly 100 is permanently secured to handpiece assembly 200.

Figure 2A:
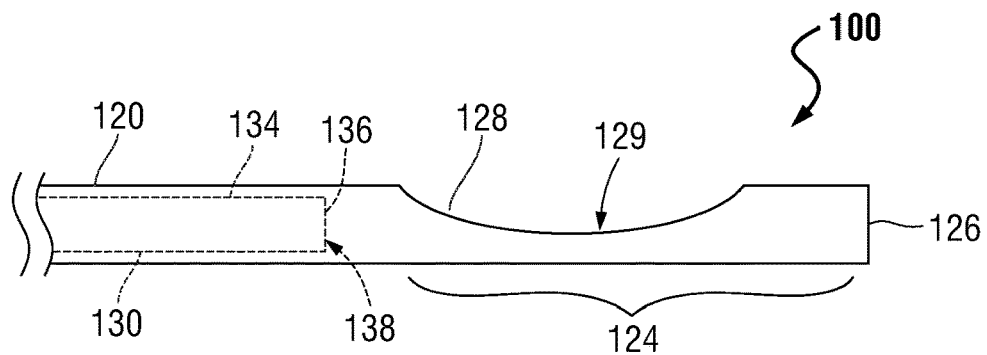
FIGS. 2A and 2B are side views of a distal portion of an end effector assembly of the tissue resecting instrument of FIG. 1 with an inner cutting shaft of the end effector assembly disposed in more-proximal and more-distal positions, respectively.
Figure 2B:
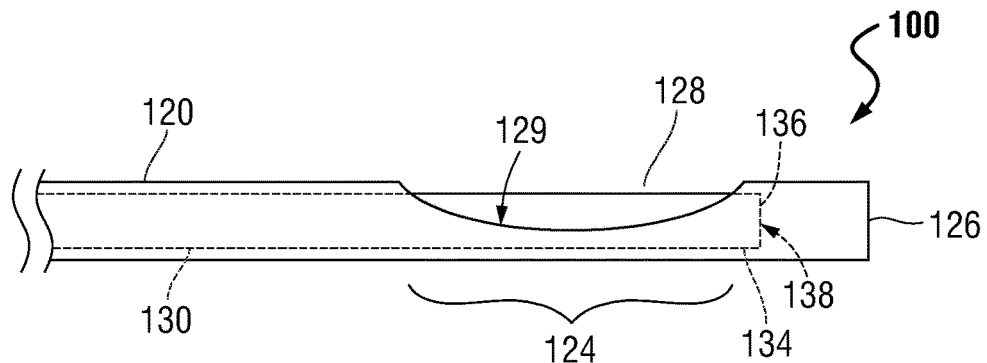
Figure 4:
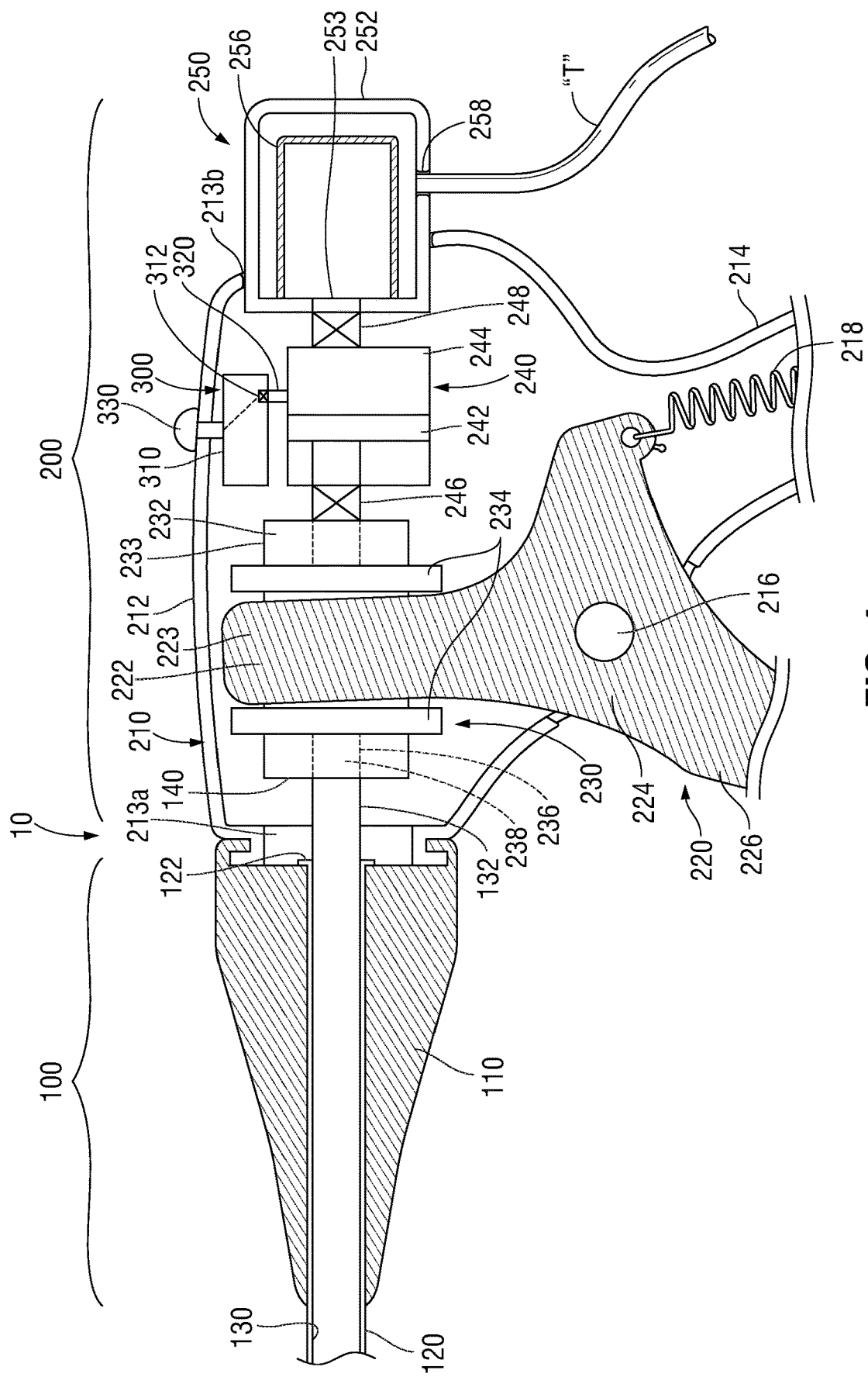
FIG. 4 is a longitudinal, cross-sectional view of the proximal portion of the tissue resecting instrument of FIG. 1 including an auxiliary vacuum feature.

Referring to FIGS. 2A, 2B, and 4, end effector assembly 100 includes a proximal hub housing 110 which may be formed as a rotation knob configured to rotatably engage handpiece assembly 200 (or may be configured to fixedly engage handpiece assembly 200), an outer shaft 120 fixedly engaged with and extending distally from proximal hub housing 110, an inner cutting shaft 130 movable disposed within outer shaft 120, and an inner drive hub 140 coupled to inner cutting shaft 130 such that movement imparted to inner drive hub 140, e.g., via handpiece assembly 200, as detailed below, drives translation and, in embodiments, translation and/or rotation, of inner cutting shaft 130 within and relative to outer shaft 120.

Outer shaft 120 of end effector assembly 100, includes a proximal end portion 122 fixedly engaged with proximal hub housing 110. Outer shaft 120 further includes a distal end portion 124 defining a closed distal end 126 and a window 128 proximally-spaced from closed distal end 126. Window 128 provides access to the interior of outer shaft 120 and may be surrounded by a cutting edge 129 about the outer perimeter of window 128 so as to facilitate cutting of tissue passing through window 128 and into outer shaft 120.

Inner cutting shaft 130 defines a proximal end portion 132 and a distal end portion 134 defining an open distal end 136. Inner cutting shaft 130 defines an annular cutting edge 138 surrounding open distal end 136 so as to facilitate cutting of tissue passing into inner cutting shaft 130 via open distal end 136. Inner cutting shaft 130 is translatable and, in embodiments, translatable and/or rotatable, within and relative to outer shaft 120. More specifically, inner cutting shaft 130 is configured to translate distally and proximally in a reciprocating motion such that annular cutting edge 138 is exposed within window 128 of outer shaft 120 during at least a portion of the reciprocation motion of inner cutting shaft 130 to enable cutting of tissue extending through window 128. As detailed below, suction is provided to facilitate drawing tissue into window 128 and, thus, cutting and removal of tissue through inner cutting shaft 130. Inner drive hub 140 is engaged about proximal end portion 132 of inner cutting shaft 130.

Figure 3A:
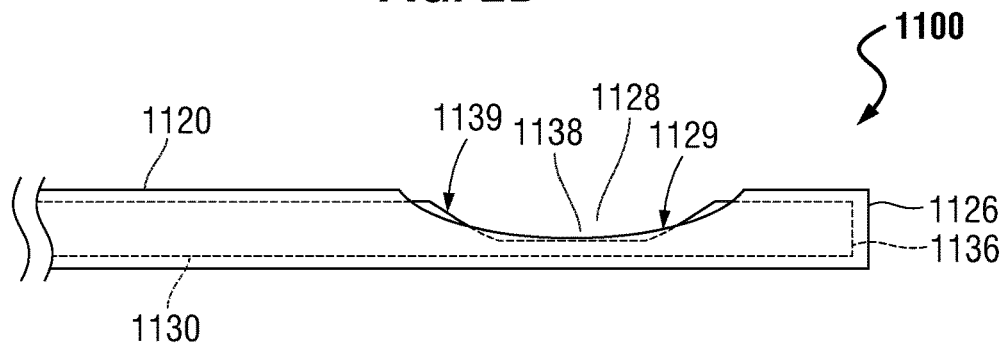
FIGS. 3A and 3B are side views of a distal portion of another end effector assembly configured for use with the tissue resecting instrument of FIG. 1 with an inner cutting shaft of the end effector assembly disposed in first and second rotational positions, respectively.
Figure 3B:
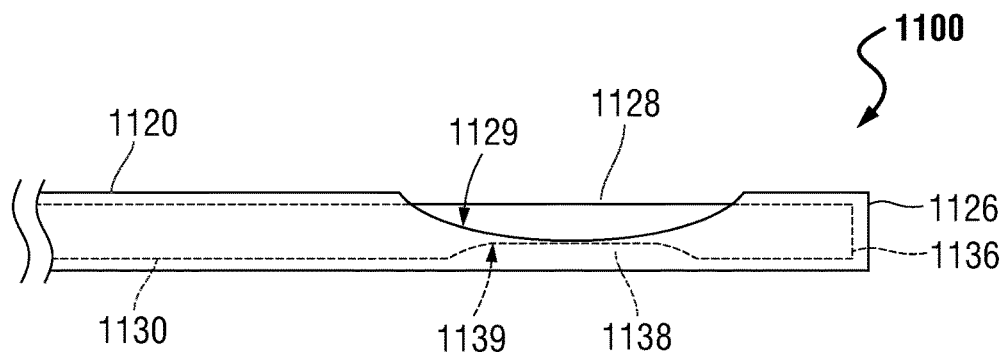

With momentary reference to FIGS. 3A and 3B, another embodiment of an end effector assembly 1100 configured for use with tissue resecting instrument 10 (FIG. 1) is shown. End effector assembly 1100 is similar to and may include any of the features of end effector assembly 100 (FIGS. 2A-2B), except that, rather than providing reciprocation (and, in embodiments, rotation), inner cutting shaft 1130 of end effector assembly 1100 is longitudinally fixed and rotatable relative to outer shaft 1120. End effector assembly 1100 further differs from end effector assembly 100 (FIG. 2A) in that outer shaft 1120 and inner cutting shaft 1130 both define window 1128, 1138 proximally-spaced from the respective distal end 1126, 1136 thereof. Window 1128 and/or window 1138 may be surrounded by a cutting edge 1129, 1139, respectively, configured to facilitate cutting of tissue passing through windows 1128, 1138 upon relative rotation between windows 1128, 1138, e.g., as a result of rotation of inner cutting shaft 1130 relative to outer shaft 1120. Other suitable end effector assemblies including various different outer shaft and inner cutting shaft configurations are also contemplated.

Referring to FIGS. 1 and 4, handpiece assembly 200 generally includes a handle housing 210, a trigger 220 pivotably coupled to handle housing 210, a drive assembly 230 disposed within handle housing 210 and operably coupled to trigger 220, a vacuum generator 240 disposed within handle housing 210 and operably coupled to drive assembly 230, and a tissue collection cartridge 250 releasably coupled to handle housing 210 (although in other embodiments tissue collection cartridge is permanently coupled to handle housing 210) and operably coupled to vacuum generator 240. Outflow tubing "T" couples tissue collection cartridge 250 to the fluid collection reservoir (not shown) for collecting fluid suctioned through tissue resecting instrument 10 during use. Alternatively, as noted above, handle housing 210 may include internal outflow tubing and an internal fluid collection reservoir (not shown) coupled to tissue collection cartridge 250 to retain the fluid suctioned through tissue resecting instrument 10 during use within tissue resecting instrument 10. Further, as also noted above, tissue resecting instrument 10 may be configured for powered actuation and, in such embodiments, a motor and one or more actuation buttons (not shown) replaces trigger 220. Other suitable powered or manual actuators are also contemplated.

Handle housing 210 defines a pistol-grip configuration, although other configurations are also contemplated, and includes a barrel portion 212 and a fixed handle portion 214 depending from barrel portion 212. Barrel portion 212 includes a distal port 213a about which proximal hub housing 110 of end effector assembly 100 is configured to releasably engage handle housing 210, e.g., via snap-fit engagement, with inner cutting shaft 130 and inner drive hub 140 extending through distal port 213a into handle housing 210. Barrel portion 212 also includes a proximal port 213b configured to receive (releasably or permanently) at least a portion of tissue collection cartridge 250, e.g., in threaded engagement, friction-fit engagement, etc. Barrel portion 212 of handle housing 210 houses drive assembly 230 and vacuum generator 240 therein.

Handle housing 210 supports a pivot 216 therein about which trigger 220 is pivotably coupled, thereby enabling trigger 220 to pivot relative to fixed handle portion 214 of handle housing 210 through an actuation stroke between an un-actuated position, wherein trigger 220 is further-spaced from fixed handle portion 214, and an actuated position, wherein trigger 220 is closer to fixed handle portion 214. The actuation stroke of trigger 220 includes a forward stroke portion involving movement of trigger 220 from the un-actuated position to the actuated position, and a return stroke portion, involving movement of trigger 220 from the actuated position back to the un-actuated position. Fixed handle portion 214 retains a first end (not shown) of a biasing member 218, e.g., an extension spring, in fixed position relative to fixed handle portion 214. A second end of biasing member 218 is engaged with trigger 220 such that biasing member 218 biases trigger 220 towards the un-actuated position.

Trigger 220 includes an upper drive portion 222, an intermediate pivot portion 224, and a lower manipulation portion 226, and may be formed as a single, monolithic piece or may otherwise be formed as a unitary structure. Intermediate pivot portion 224 of trigger 220 is pivotably coupled to handle housing 210 about pivot 216. Upper drive portion 222 of trigger 220 extends upwardly from intermediate pivot portion 224 into handle housing 210 to operably couple to drive assembly 230. More specifically, upper drive portion 222 defines a bifurcated configuration including a pair of spaced-apart upper drive flanges 223 disposed on either side of drive assembly 230 and operably coupled thereto. Lower manipulation portion 226 of trigger 220 extends downwardly from intermediate pivot portion 224 exteriorly from handle housing 210 to enable manual manipulation thereof by a user between the un-actuated and actuated positions.

Drive assembly 230 of handpiece assembly 200 includes a mandrel 232 engaged about an inner shaft 236 defining a lumen 238 extending therethrough. Mandrel 232 includes a body 233 and pair of longitudinally-spaced rims 234 disposed on body 233 and is configured to receive upper drive flanges 223 of upper drive portion 222 of trigger 220 longitudinally between rims 234 on either side of body 233.

In this manner, pivoting of trigger 220 towards the actuated position urges upper drive flanges 223 into the distal rim of the pair of longitudinally-spaced rims 234 to thereby urge mandrel 232 distally through handle housing 210. On the other hand, pivoting of trigger 220 towards the un-actuated position urges drive flanges 223 into the proximal rim of the pair of longitudinally-spaced rims 234 to thereby urge mandrel 232 proximally through handle housing 210.

Inner drive hub 140 of end effector assembly 100 is configured to releasably engage mandrel 232, e.g., via mechanical fastening, friction-fit engagement, magnetic coupling, etc., upon engagement of end effector assembly 100 with handpiece assembly 200 such that inner drive hub 140 is fixed relative to mandrel 232, and such that the interior of inner cutting shaft 130 of end effector assembly 100 is disposed in fluid communication with lumen 238 of inner shaft 236. Of course, in embodiments where end effector assembly 100 is permanently secured to handpiece assembly 200, inner drive hub 140 of end effector assembly 100 is permanently engaged to mandrel 232.

With inner drive hub 140 fixed relative to mandrel 232, translation of mandrel 232, e.g., in response to pivoting of trigger 220, likewise translates inner cutting shaft 130 through and relative to outer shaft 120. More specifically, pivoting of trigger 220 relative to handle housing 210 between the un-actuated position and the actuated position translates inner cutting shaft 130 through and relative to outer shaft 120 between a more-proximal position (FIG. 2A) and a more-distal position (FIG. 2B).

With momentary additional reference to FIGS. 3A and 3B, in embodiments where the end effector assembly, e.g., end effector assembly 1100, includes an inner cutting shaft 1130 configured to rotate relative to the outer shaft 1120, rather than inner drive hub 140 being fixed relative to mandrel 232, mandrel 232 may include a coupler (not shown) that is operably engaged within a helical channel (not shown) defined on or otherwise associated with inner drive hub 140. As a result of such a configuration, longitudinal translation of mandrel 232, e.g., in response to actuation of trigger 220, effects rotation of inner drive hub 140 and, thus, inner cutting shaft 1130.

In embodiments where the end effector assembly, e.g., end effector assembly 1100, includes an inner cutting shaft 1130 configured to both reciprocate and rotate relative to the outer shaft 1120, rather than inner drive hub 140 being fixed relative to mandrel 232, mandrel 232 or inner drive hub 140 may include a helical channel (not shown) defined thereon or otherwise associated therewith and a coupler (not shown) may be fixed within handle housing 210 and engaged within the helical channel. As a result of such a configuration, longitudinal translation of mandrel 232, e.g., in response to actuation of trigger 220, effects both rotation and translation of inner drive hub 140 and, thus, inner cutting shaft 1130.

Referring again to FIGS. 1 and 4, vacuum generator 240 is disposed within handle housing 210 and operably coupled to drive assembly 230. Vacuum generator 240 includes a chamber 244 that is disposed in fluid communication with lumen 238 of inner shaft 236 of drive assembly 230 which, as noted above, is disposed in fluid communication with the interior of inner cutting shaft 130 of end effector assembly 100. As a result, vacuum generated by vacuum generator 240 suctions tissue and fluid through window 128 of outer shaft 120, open distal end 136 of inner cutting shaft 130, lumen 238 of inner shaft 236 of drive assembly 230, and into chamber 244 of vacuum generator 240.

Vacuum generator 240, more specifically, includes a plunger 242 sealingly engaged and slidably disposed within chamber 244. In embodiments, inner shaft 236 defines the push-rod of plunger 242, although other configurations are also contemplated. Plunger 242 is coupled with mandrel 232, e.g., via inner shaft 236 or in any other suitable manner, such that as mandrel 232 is translated through handle housing 210, plunger 242 is similarly translated through chamber 244. More specifically, when mandrel 232 is translated distally, e.g., in response to movement of trigger 220 from the un-actuated position towards the actuated position to move inner cutting shaft 130 from the more-proximal position (FIG. 2A) towards the more-distal position (FIG. 2B), plunger 242 is moved distally through chamber 244 to increase the volume of chamber 244 and generate vacuum within chamber 244, thereby establishing suction through lumen 238 of inner shaft 236 and inner cutting shaft 130. In this manner, as inner cutting shaft 130 is moved from the more-proximal position (FIG. 2A) towards the more-distal position (FIG. 2B), tissue and fluid are suctioned through window 128 of outer shaft 120, tissue is cut by open distal end 136 of inner cutting shaft 130, and the cut tissue and fluid are suctioned proximally through lumen 238 of inner shaft 236 of drive assembly 230 and into chamber 244 of vacuum generator 240.

When mandrel 232 is returned proximally, e.g., in response to movement of trigger 220 from the actuated position back towards the un-actuated position to move inner cutting shaft 130 from the more-distal position (FIG. 2B) back towards the more-proximal position (FIG. 2A), plunger 242 is moved proximally through chamber 244 to push tissue and fluid, under pressure, from chamber 244 of vacuum generator 240 into tissue collection cartridge 250. One-way valves 246, 248 are disposed between vacuum generator 240 and drive assembly 230 and between vacuum generator 240 and tissue collection cartridge 250, respectively, to inhibit pumping tissue and fluid distally from vacuum generator 240 into lumen 238 of inner shaft 236 and drawing tissue and fluid distally from tissue collection cartridge 250 back into vacuum generator 240, respectively.

Tissue collection cartridge 250, as noted above, is releasably coupled to handle housing 210. Tissue collection cartridge 250, more specifically, may be configured to releasably engage proximal port 213b of handle housing 210 via threaded engagement or other suitable engagement. Tissue collection cartridge 250 includes an outer housing 252 defining a distal port 253 configured to couple, in fluid communication, with chamber 244 of vacuum generator 240 upon engagement of tissue collection cartridge 250 with handle housing 210. In this manner, tissue and fluid suctioned through window 128 of outer shaft 120, open distal end 136 of inner cutting shaft 130, lumen 238 of inner shaft 236 of drive assembly 230, and into chamber 244 of vacuum generator 240, may then be urged into tissue collection cartridge 250. One-way valve 248, as an alternative to being part of vacuum generator 240, may be disposed within distal port 253 of tissue collection cartridge 250.

Tissue collection cartridge 250 further includes an internal filter 256 disposed within outer housing 252 that is configured to permit passage of fluid therethrough but inhibit the passage of tissue therethrough. An outflow port 258 configured to enable connection of outflow tubing "T" with tissue collection cartridge 250 enables the fluid that passes through filter 256 to drain out from tissue collection cartridge 250 to a fluid collection reservoir (not shown).

Referring generally to FIGS. 1-2B and 4, in preparation for use, if not already done so, end effector assembly 100 is engaged with handpiece assembly 200, tissue collection cartridge 250 is engaged with handle housing 210 of handpiece assembly 200, and outflow tubing "T" is coupled between tissue collection cartridge 250 and the fluid collection reservoir (not shown). In embodiments, any or all of the above engagements and/or couplings are accomplished during manufacturing and, thus, need not be performed by the end-user.

With tissue resecting instrument 10 assembled as detailed above, in use, tissue resecting instrument 10 is inserted into an internal body cavity or organ, e.g., a uterus, such that the distal end portion of end effector assembly 100 is positioned adjacent tissue to be removed. Tissue resecting instrument 10 may be inserted through an endoscope, e.g., a hysteroscope, or other instrument, or may be used independently. Once tissue resecting instrument 10 is positioned as desired adjacent tissue to be removed, tissue resecting instrument 10 is activated by pivoting trigger 220 relative to fixed handle portion 214 of handle housing 210 through the actuation stroke from the un-actuated position to the actuated position and back to the un-actuated position to thereby reciprocate inner cutting shaft 130 through and relative to outer shaft 120 (e.g., from the more-proximal position (FIG. 2A) to the more-distal position (FIG. 2B) and back to the more-proximal position (FIG. 2A)), suction cut tissue and fluid through inner cutting shaft 130 and lumen 238 of inner shaft 236 into vacuum generator 240, and urge tissue and fluid from vacuum generator 240 into tissue collection cartridge 250. Tissue resecting instrument 10 may be repeatedly actuated as detailed above to cut and remove target tissue as desired. The tissue urged into tissue collection cartridge 250 during use is retained therein, while the fluid urged into tissue collection cartridge 250 passes through filter 256, outflow port 258, and outflow tubing "T" to the fluid collection reservoir (not shown).

Once the desired tissue is removed, tissue resecting instrument 10 may be removed from the surgical site. Thereafter, end effector assembly 100 and tissue collection cartridge 250 may be disengaged from handpiece assembly 200. End effector assembly 100 and/or handpiece assembly 200 may then be discarded, sent for reprocessing, or sterilized for reuse. Tissue collection cartridge 250 may be sent to pathology for analyzing the tissue retained therein or may likewise be discarded.

Referring again to FIG. 4, in embodiments, tissue resecting instrument 10 further includes an auxiliary vacuum feature in the form of a vacuum accumulator 300. Vacuum accumulator 300 includes an accumulator tank 310 disposed within handle housing 210, a fluid line 320 fluidly coupling accumulator tank 310 with chamber 244 of vacuum generator 240 within handle housing 210, and a release actuator 330 operably coupled with accumulator tank 310 and extending from handle housing 210 to enable selective actuation thereof by a user.

Accumulator tank 310 of vacuum accumulator 300 is configured to incrementally accumulate vacuum therein during use. More specifically, as mandrel 232 is translated distally, e.g., in response to movement of trigger 220 from the un-actuated position towards the actuated position to move inner cutting shaft 130 from the more-proximal position (FIG. 2A) towards the more-distal position (FIG. 2B), plunger 242 is moved distally through chamber 244 to increase the volume of chamber 244 and generate vacuum within chamber 244 and, likewise, generate vacuum within accumulator tank 310 due to the fluid coupling of accumulator tank 310 with chamber 244 via fluid line 320. A manipulatable valve 312 disposed within accumulator tank 310 functions, in a first position thereof, as a one-way valve to inhibit the release of vacuum from accumulator tank 310 and, thus, upon each actuation of tissue resecting instrument 10 to translate plunger 242 distally through chamber 244, vacuum is accumulated within accumulator tank 310. Manipulatable valve 312 may be biased towards the first position.

Release actuator 330 is operably coupled to manipulatable valve 312 such that actuation of release actuator 330 transitions manipulatable valve 312 from the first position, wherein manipulatable valve 312 functions as a one-way valve, to a second position, wherein manipulatable valve 312 defines a bi-directional, open configuration. The bias of manipulatable valve 312 towards the first position may maintain or return manipulatable valve 312 to the first position when release actuator 330 is not actuated, or may be configured in any other suitable manner. Additionally or alternatively, release actuator 330 may be biased towards an un-actuated position, wherein release actuator 330 protrudes further from handle housing 210. In such embodiments, release actuator 330 is depressed towards handle housing 210 to the actuated position to thereby transition manipulatable valve 312 to the second position. Other suitable configurations of release actuator 330 are also contemplated.

As noted above, upon each actuation of tissue resecting instrument 10, vacuum is incrementally accumulated within accumulator tank 310. When it is desired to provide increased suction through inner cutting shaft 130, release actuator 330 may be depressed to open manipulatable valve 312, thereby supplementing the suction provided by vacuum generator 240 with additional suction provided by vacuum accumulator 300. In this manner, the user may selectively provide increased suction through inner cutting shaft 130 as desired during a procedure.

Figure 5:
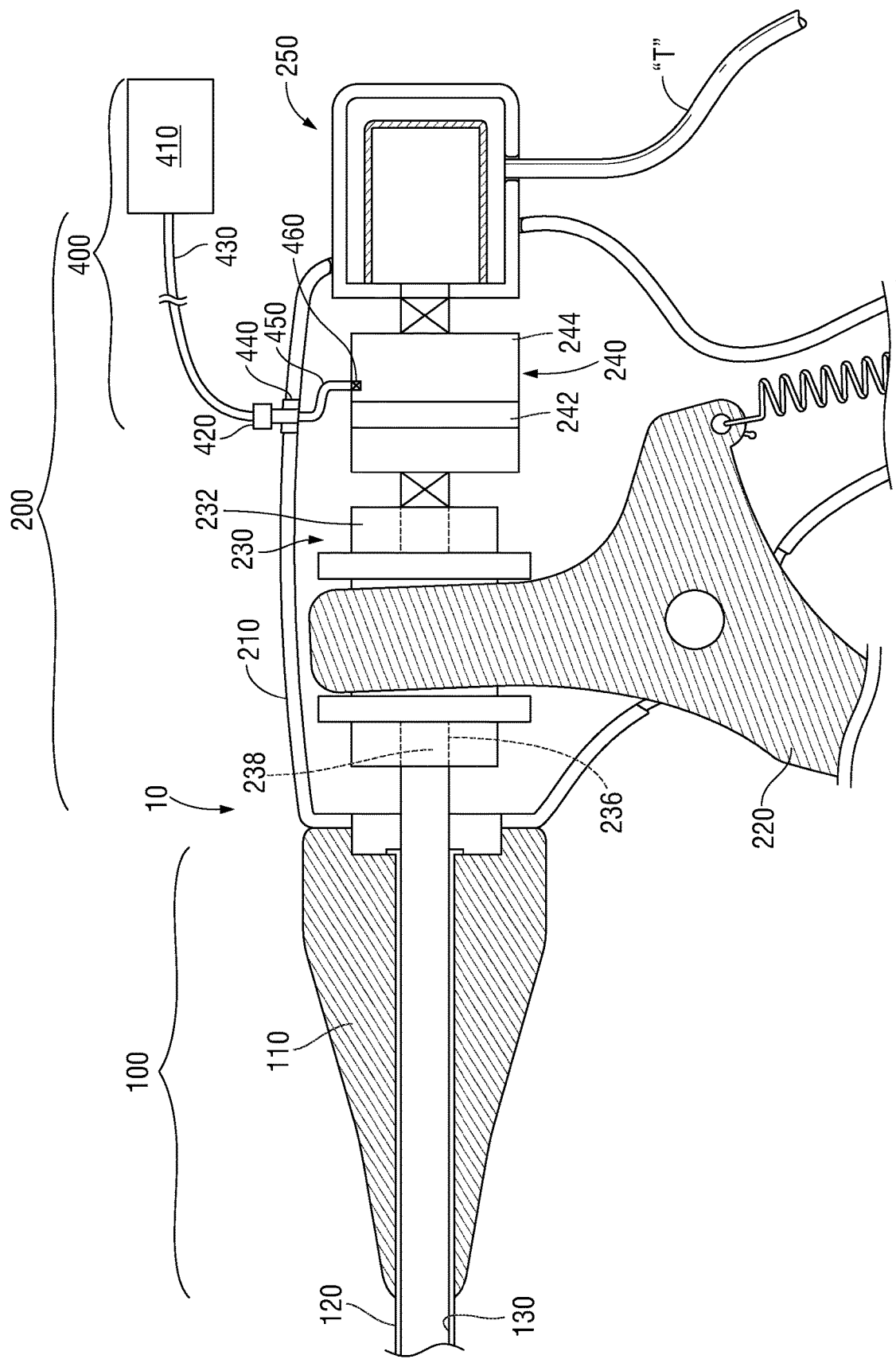
FIG. 5 is a longitudinal, cross-sectional view of the proximal portion of the tissue resecting instrument of FIG. 1 including another auxiliary vacuum feature.

Referring to FIG. 5, in embodiments, tissue resecting instrument 10 additionally or alternatively includes an auxiliary vacuum feature in the form of a supplemental vacuum generator 400. Supplemental vacuum generator 400 includes a vacuum source 410, e.g., a vacuum pump, a first connector 420, and a fluid line 430 extending between and fluidly coupling vacuum source 410 and first connector 420. Vacuum source 410 may be positioned remote from tissue resecting instrument 10, e.g., on a surgical cart, may be positioned in closer proximity to tissue resecting instrument 10, e.g., worn on a user or held by a user or support personnel, or may be disposed on handle housing 210 of tissue resecting instrument 10, e.g., releasably engagable therewith such as, for example, via slide-track engagement, snap-fit engagement, etc. First connector 420 is configured for releasable coupling with a second connector 440 disposed on and extending through handle housing 210. First and second connectors 420, 440, respectively, may be configured to releasably couple to one another in any suitable manner, e.g., friction-fitting, twist-lock, snap-fit, etc., to readily enable engagement of supplemental vacuum generator 400 with tissue resecting instrument 10 when desired for use therewith and disengagement of supplemental vacuum generator 400 from tissue resecting instrument 10 when not desired for use therewith. In embodiments where vacuum source 410 is disposed on handle housing 210 of tissue resecting instrument 10, engagement of vacuum source 410 with handle housing 210 may also result in coupling of first and second connectors 420, 440, respectively, with one another.

Handle housing 210 of tissue resecting instrument 10 includes an internal fluid line 450 fluidly coupled between second connector 440 and chamber 244 of vacuum generator 240. In embodiments, a one-way valve 460 is disposed between vacuum generator 240 and second connector 440 to inhibit fluid flow from vacuum generator 240 to second connector 440 and, thus, to supplemental vacuum generator 400.

During use, as noted above, upon each actuation of tissue resecting instrument 10, vacuum is generated via vacuum generator 240 to provide suction through inner cutting shaft 130, thus enabling cut tissue and fluid to be suctioned proximally through tissue resecting instrument 10 and, ultimately, urged into tissue collection cartridge 250. In some instances, it may be desirable to provide increased suction, e.g., suction beyond the capability of vacuum generator 240. In such instances, supplemental vacuum generator 400 may be coupled to tissue resecting instrument 10 and activated to provide additional suction within chamber 244 of vacuum generator 240, thus increasing the suction through inner cutting shaft 130. Vacuum source 410 may be configured to provide on-demand suction and/or controlled suction according to a suction profile, e.g., intermittent suction at suitable intervals, intermittent suction correlated with actuation of trigger 220, etc. However, even with supplemental vacuum generator 400 coupled to tissue resecting instrument 10, the additional suction provided thereby need not be utilized. That is, supplemental vacuum generator 400 may be coupled to tissue resecting instrument 10 and only activated if and when necessary to provide additional suction.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue resecting instrument, comprising:
   a housing;
   an outer shaft extending distally from the housing and defining a window at a distal end portion thereof;
   an inner cutting shaft extending through the outer shaft, the inner cutting shaft at least one of translatable or rotatable relative to the outer shaft to cut tissue extending through the window;
   a drive assembly coupled to the inner cutting shaft and configured to drive the at least one of translation or rotation of the inner cutting shaft;
   a trigger coupled to the drive assembly, wherein manual actuation of the trigger actuates the drive assembly to drive the at least one of translation or rotation of the inner cutting shaft;
   a vacuum generator coupled to the drive assembly and the inner cutting shaft such that, during a first portion of the actuation of the drive assembly, the vacuum generator is configured to generate vacuum to suction cut tissue through the inner cutting shaft and into the vacuum generator;
   a tissue collection cartridge configured to releasably engage the housing, the tissue collection cartridge defining a port configured to communicate with the vacuum generator such that, during a second portion of the actuation of the drive assembly, the vacuum generator urges cut tissue from the vacuum generator through the port into the tissue collection cartridge; and an auxiliary vacuum source configured to selectively provide additional vacuum to increase suctioning of cut tissue through the inner cutting shaft and into the vacuum generator.

2. The tissue resecting instrument according to claim 1, wherein the trigger is pivotably coupled to the housing and movable relative thereto between an un-actuated position and an actuated position to drive the drive assembly to translate the inner cutting shaft between a more-proximal position and a more-distal position.

3. The tissue resecting instrument according to claim 2, wherein the first portion of the actuation of the drive assembly corresponds to movement of the trigger from the un-actuated position to the actuated position, and wherein the second portion of the actuation of the drive assembly corresponds to movement of the trigger from the actuated position to the un-actuated position.

4. The tissue resecting instrument according to claim 1, wherein the auxiliary vacuum source is disposed on or within the housing.

5. The tissue resecting instrument according to claim 1, wherein the auxiliary vacuum source is configured to releasably couple to the housing.

6. The tissue resecting instrument according to claim 1, wherein the auxiliary vacuum source includes a vacuum accumulator.

7. The tissue resecting instrument according to claim 1, wherein the auxiliary vacuum source includes a vacuum pump.

8. A tissue resecting instrument, comprising:

a housing;

an outer shaft extending distally from the housing and defining a window at a distal end portion thereof;

an inner cutting shaft extending through the outer shaft, the inner cutting shaft at least one of translatable or rotatable relative to the outer shaft to cut tissue extending through the window;

a drive assembly coupled to the inner cutting shaft and configured to drive the at least one of translation or rotation of the inner cutting shaft;

a trigger coupled to the drive assembly, wherein manual actuation of the trigger actuates the drive assembly to drive the at least one of translation or rotation of the inner cutting shaft;

a vacuum generator coupled to the drive assembly and the inner cutting shaft such that, during a first portion of the actuation of the drive assembly, the vacuum generator is configured to generate vacuum to suction cut tissue through the inner cutting shaft and into the vacuum generator;

a tissue collection cartridge configured to engage the housing, the tissue collection cartridge defining a port configured to communicate with the vacuum generator such that, during a second portion of the actuation of the drive assembly, the vacuum generator urges cut tissue from the vacuum generator through the port into the tissue collection cartridge; and a vacuum accumulator coupled to the vacuum generator and configured to accumulate vacuum, wherein the vacuum accumulator is configured to selectively release the accumulated vacuum to provide additional vacuum to increase suctioning of cut tissue through the inner cutting shaft and into the vacuum generator.

9. The tissue resecting instrument according to claim 8, wherein the trigger is pivotably coupled to the housing and movable relative thereto between an un-actuated position and an actuated position to drive the drive assembly to translate the inner cutting shaft between a more-proximal position and a more-distal position.

10. The tissue resecting instrument according to claim 9, wherein the first portion of the actuation of the drive assembly corresponds to movement of the trigger from the un-actuated position to the actuated position, and wherein the second portion of the actuation of the drive assembly corresponds to movement of the trigger from the actuated position to the un-actuated position.

11. The tissue resecting instrument according to claim 8, wherein the vacuum accumulator includes an accumulator tank configured to accumulate vacuum therein and a release actuator configured to release the accumulated vacuum to provide the additional vacuum.

12. The tissue resecting instrument according to claim 11, wherein a manipulatable valve is disposed between the accumulator tank and the vacuum generator and wherein the release actuator is configured to transition the manipulatable valve to a bi-directional, open configuration to provide the additional vacuum.

13. The tissue resecting instrument according to claim 8, wherein the vacuum accumulator is configured to incrementally accumulate vacuum upon each actuation of the drive assembly.

14. A tissue resecting instrument, comprising:

a housing;

an outer shaft extending distally from the housing and defining a window at a distal end portion thereof;

an inner cutting shaft extending through the outer shaft, the inner cutting shaft at least one of translatable or rotatable relative to the outer shaft to cut tissue extending through the window;

a drive assembly coupled to the inner cutting shaft and configured to drive the at least one of translation or rotation of the inner cutting shaft;

a trigger coupled to the drive assembly, wherein manual actuation of the trigger actuates the drive assembly to drive the at least one of translation or rotation of the inner cutting shaft;

a vacuum generator coupled to the drive assembly and the inner cutting shaft such that, during a first portion of the actuation of the drive assembly, the vacuum generator is configured to generate vacuum to suction cut tissue through the inner cutting shaft and into the vacuum generator;

a tissue collection cartridge configured to releasably engage the housing, the tissue collection cartridge defining a port configured to communicate with the vacuum generator such that, during a second portion of the actuation of the drive assembly, the vacuum generator urges cut tissue from the vacuum generator through the port into the tissue collection cartridge; and a supplemental vacuum configured to releasably couple to the vacuum generator, the supplemental vacuum selectively activatable to provide additional vacuum to increase suctioning of cut tissue through the inner cutting shaft and into the vacuum generator.

15. The tissue resecting instrument according to claim 14, wherein the trigger is pivotably coupled to the housing and movable relative thereto between an un-actuated position and an actuated position to drive the drive assembly to translate the inner cutting shaft between a more-proximal position and a more-distal position.

16. The tissue resecting instrument according to claim 15, wherein the first portion of the actuation of the drive assembly corresponds to movement of the trigger from the un-actuated position to the actuated position, and wherein the second portion of the actuation of the drive assembly corresponds to movement of the trigger from the actuated position to the un-actuated position.

17. The tissue resecting instrument according to claim 14, wherein the supplemental vacuum includes a vacuum pump.

18. The tissue resecting instrument according to claim 17, wherein the supplemental vacuum further includes a fluid line extending from the vacuum pump to a first connector, the first connector configured to releasably couple to a second connector associated with the housing to thereby couple the vacuum pump with the vacuum generator.

19. The tissue resecting instrument according to claim 14, further comprising a one-way valve disposed between the supplemental vacuum and the vacuum generator.

20. The tissue resecting instrument according to claim 14, wherein the supplemental vacuum is configured to provide the additional vacuum to the chamber of the vacuum generator.

* * * * *